United States Patent
Taira

(10) Patent No.: US 7,076,995 B2
(45) Date of Patent: Jul. 18, 2006

(54) METHOD FOR DETERMINING REUSABILITY OF REFRIGERANT USING EQUIPMENT OR REFRIGERANT LINES, AND REUSABILITY CHECK TOOL FOR REFRIGERANT USING EQUIPMENT OR REFRIGERANT LINES

(75) Inventor: Shigeharu Taira, Kusatsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/501,553

(22) PCT Filed: Feb. 5, 2003

(86) PCT No.: PCT/JP03/01205

§ 371 (c)(1),
(2), (4) Date: Jul. 16, 2004

(87) PCT Pub. No.: WO03/067163

PCT Pub. Date: Aug. 14, 2003

(65) Prior Publication Data

US 2005/0081606 A1    Apr. 21, 2005

(30) Foreign Application Priority Data

Feb. 8, 2002 (JP) .............................. 2002-032831
Feb. 8, 2002 (JP) .............................. 2002-032832

(51) Int. Cl.
*G01N 33/00* (2006.01)
(52) U.S. Cl. .................................................. 73/61.41
(58) Field of Classification Search ............... 73/53.01; 116/206; 62/125
See application file for complete search history.

(56) References Cited

U.S. PATENT DOCUMENTS

| 4,248,597 | A | * | 2/1981 | McNeely .................... 116/206 |
| 4,923,806 | A | * | 5/1990 | Klodowski .................. 436/39 |
| 5,831,144 | A | * | 11/1998 | Pastorello .................. 73/23.2 |
| 5,846,833 | A | * | 12/1998 | Clough et al. .............. 436/139 |
| 2003/0010044 | A1 | | 1/2003 | Taira |

FOREIGN PATENT DOCUMENTS

| JP | H2-146588 U | 12/1990 |
| JP | 11-325621 A | 11/1999 |
| JP | 2001-133566 A | 5/2001 |
| JP | 2001-227846 A | 8/2001 |

* cited by examiner

*Primary Examiner*—Hezron Williams
*Assistant Examiner*—Paul M. West
(74) *Attorney, Agent, or Firm*—Global IP Counselors

(57) ABSTRACT

The present invention provides a simple determination method with regard to the reusability of refrigerant using equipment or refrigerant lines toward the goal of reusing refrigerant using equipment or refrigerant lines. The method of determining the reusability of refrigerant using equipment or refrigerant lines includes a first step and a second step. In the first step, residual material remaining inside refrigerant using equipment or refrigerant lines is applied to a check sheet. In the second step, a determination with regard to the reusability of the refrigerant using equipment or the refrigerant lines is performed based upon the color of the check sheet on which the residual material was applied.

9 Claims, 3 Drawing Sheets

ME THOD FOR DETERMINING
REUSABILITY OF REFRIGERANT USING
EQUIPMENT OR REFRIGERANT LINES,
AND REUSABILITY CHECK TOOL FOR
REFRIGERANT USING EQUIPMENT OR
REFRIGERANT LINES

TECHNICAL FIELD

The present invention relates to a method for determining the reusability of refrigerant using equipment or refrigerant lines and to a reusability check tool for refrigerant using equipment or refrigerant lines.

BACKGROUND ART

Because the damage to the ozone layer has become a problem in recent years, the use of HCFCs as refrigerants has recently begun to be reduced as a step toward the goal of their complete elimination. Hereafter, the gradual reduction of HCFC type refrigerants (HCFC-22 and the like) will continue worldwide, and it will be necessary instead to use substitute refrigerants such as HFC type refrigerants and the like.

In this situation, there are an increasing number of cases in which previously installed refrigerant using equipment (such as air conditioners and the like) is modified in order to use a substitute refrigerant.

In addition, with multi-type air conditioners that are installed inside structures such as apartment buildings, office buildings, and the like, and with air conditioners that air condition the entire space inside a residential home (housing air conditioners), the refrigerant lines that connect the outdoor unit with the indoor units are embedded in the walls or extend over the rear surface of the ceiling. In this type of situation, in order to dismantle the preexisting air conditioner and install a new air conditioner, whether or not the preexisting refrigerant lines can be appropriated (reused) with the new air conditioner is an important factor in the cost of installation. This is because the task of replacing the preexisting lines will take a great deal of time and cost a great deal of money. In addition, even if the preexisting lines can be appropriated, whether or not it will be necessary to clean the preexisting lines will be a factor in reducing the installation costs.

Generally, refrigerator oil that contains impurities will remain adhered to the preexisting lines. If the fouling from the remaining oil is severe, there is a strong possibility that the remaining impurities will infiltrate the new refrigerant to be used, the decompressor that is the expansion mechanism (an expansion valve or a capillary tube) will become clogged and will cease operating, and the refrigerant oil will deteriorate. In particular, refrigerant oils that are used with HFC type refrigerants are synthetic oils such as ether oil or ester oil, and easily dissolve the impurities in the preexisting lines because of their high polarity. Thus, when using HFC type refrigerants in new air conditioners, there is a strong possibility that problems may occur in the decompressor of the new air conditioner due to the remaining impurities in the preexisting lines.

Thus at present, a cleaner will be employed to clean the interior of the lines when one attempts to appropriate preexisting lines that have been used for 10–20 years.

However, a cleaner that cleans preexisting lines is extremely expensive, and moreover, the cost of cleaning is not cheap.

On the other hand, cleaning is not necessary when there is little fouling of the preexisting lines. There are also cases in which the fouling of the preexisting lines will be reduced, and the need for cleaning will be eliminated, due to the method by which the refrigerant and the oil are recovered.

However, obtaining a sample of the residual material inside the preexisting lines, bringing it to a research lab or the like, and examining the oil or refrigerant in the preexisting lines has, in the past, cost more than the cost of cleaning. Because of this, manufacturers currently unconditionally recommend in most cases that the preexisting lines be cleaned with a cleaning device.

When there is no need for cleaning, it is preferable that the preexisting refrigerant lines (preexisting lines) be reused as is.

In addition, it is preferable that uninstalled refrigerant using equipment be reused to the greatest extent possible due to environmental concerns. Preexisting equipment includes that which can be reused if cleaned, and that which can be reused if some of the components thereof (such as the compressor and the like) are replaced.

SUMMARY OF THE INVENTION

An object of the present invention is to provide a method of easily determining the reusability of refrigerant using equipment or refrigerant lines for the purpose of reusing the refrigerant using equipment or the refrigerant lines.

According to a first aspect of the present invention, a method that determines the reusability of refrigerant using equipment or refrigerant lines includes a first step and a second step. In the first step, residual material that remains inside refrigerant using equipment or refrigerant lines is applied to a check tool. In the second step, the reusability of the refrigerant using equipment or the refrigerant lines will be determined based upon the color of the check tool on which the residual material was applied.

The present inventors collected a large number of samples of residual material from inside refrigerant using equipment and refrigerant lines that are to be replaced or reused, and have discovered that the determination of whether or not the refrigerant using equipment or the refrigerant lines can be reused or whether or not cleaning is needed can be determined by means of the color of residual material such as residual oil and the like.

Then, the present inventors discovered that by using the check tool and comparing the color of the residual material inside the refrigerant using equipment or the refrigerant lines to a sample or the like, a determination of the reusability of the refrigerant using equipment or the refrigerant lines can be performed with a high degree of accuracy.

Based on this point of view, a determination of the reusability of the refrigerant using equipment or the refrigerant lines is performed from the color of the check tool on which the residual material from the refrigerant using equipment or the refrigerant lines is applied. Thus, the check tool can be used to easily determine the reusability of refrigerant using equipment or refrigerant lines by means of color, and problems such as wasteful cleaning work performed in situations in which the interior of the refrigerant using equipment or the refrigerant lines is not particularly fouled and thus cleaning is not needed, and cleaning and reusing refrigerant using equipment despite the fact that the interiors thereof are fouled and cannot be reused even after being cleaned, will be controlled.

Note that a tool that can compare the color of residual material to a predetermined color and perform a determination relating to reusability may be used as the check tool, or a tool that can check the pH of residual material with litmus paper or the like and perform a determination relating to reusability may be used as the check tool.

According to a second aspect of the present invention, the method of determining the reusability of refrigerant using equipment or refrigerant lines of the first aspect of the present invention is provided, in which the check tool includes a first means on which the residual material will be applied, and a second means that displays a reference color that is a determination reference. Then, in the first step, the residual material is applied to the first means. In the second step, the color of the first means is compared to the reference color of the second means to perform a determination.

Here, a second means that displays a reference color that is a determination reference is provided on the check tool, and thus by comparing the color of the first means of the check tool on which residual material has been applied with the reference color of the second means, it will be extremely easy to determine the reusability of refrigerant using equipment or refrigerant lines.

Note that the first means and the second means of the check tool may be separate entities, or may be unitary.

According to a third aspect of the present invention, the method of determining the reusability of refrigerant using equipment or refrigerant lines of the second aspect of the present invention is provided, in which the second means of the check tool displays a plurality of reference colors.

Here, the second means displays a plurality of reference colors, and thus not only can it be determined whether or not refrigerant using equipment or refrigerant lines are reusable, or whether or not cleaning is needed in order to reuse the refrigerant using equipment or the refrigerant lines, but both determinations can be easily performed. In addition, other determinations regarding the reusability of refrigerant using equipment or refrigerant lines can be performed. Furthermore, it is also possible to provide a reference color in order to confirm that the refrigerant using equipment or the refrigerant lines can be reused.

According to a fourth aspect of the present invention, the method of determining the reusability of refrigerant using equipment or refrigerant lines of the third aspect of the present invention is provided in which the second means of the check tool displays a normal color and a boundary color. The normal color is a color that indicates that cleaning is unnecessary when reusing refrigerant using equipment or refrigerant lines. The boundary color is a color that is at a boundary that indicates that cleaning is necessary when reusing refrigerant using equipment or refrigerant lines.

Here, when the color of the first means to which impurities have been applied is compared to the boundary color and the color is favorable, the refrigerant using equipment or the refrigerant lines can be used without cleaning by further comparing the color of the first means to the normal color.

According to a fifth aspect of the present invention, the method of determining the reusability of refrigerant using equipment or refrigerant lines of the third aspect of the present invention is provided, in which the second means of the check tool displays a first boundary color and a second boundary color. The first boundary color is a reference color for determining whether or not there is a need to clean the refrigerant using equipment or refrigerant lines. The second boundary color is a reference color for determining whether or not it is possible to use the refrigerant using equipment or refrigerant lines.

Here, by comparing the color of the first means with the first boundary color of the second means, it can be determined whether or not it will be necessary to clean the refrigerant using equipment or refrigerant lines in order to use them. In addition, by comparing the color of the first means with the second boundary color of the second means, it can be determined whether or not it will be possible to use the refrigerant using equipment or refrigerant lines. In other words, by comparing the color of the first means and the second boundary color of the second means, it can also be determined whether or not there is a need to dispose of the refrigerant using equipment or the refrigerant lines and replace them.

According to a sixth aspect of the present invention, a check tool that is used with the method of determining the reusability of refrigerant using equipment or refrigerant lines of any of the second to fifth aspects of the present invention is provided, in which the first means and the second means are disposed near each other and are unitary.

With this check tool, the first means and the second means are disposed near each other, and thus the color of the first means and the color of the second means can be visually compared to easily perform a determination regarding the reusability of the refrigerant using equipment or refrigerant lines.

According to a seventh aspect of the present invention, the method of determining the reusability of refrigerant using equipment or refrigerant lines of the first aspect of the present invention is provided, in which the check tool is a pH analysis tool that changes color by means of an acid or an alkali. Then, in the first step, residual material is applied to the pH analysis tool. In the second step, the degree of degradation of the residual material is estimated from the color of the pH analysis tool, and a determination with regard to the reusability of the refrigerant using equipment or the refrigerant lines is performed.

Here, the check tool is a pH analysis tool, and thus when an acid or alkali is produced by the residual material of the interior of the refrigerant using equipment or the refrigerant lines, the degree of acidity or alkalinity can be easily determined from the color of the pH analysis tool. Then, the degree of degradation of the residual material of the interior of the refrigerant using equipment or the refrigerant lines can be estimated from the degree of acidity or alkalinity. It will be possible to determine the reusability of the refrigerant using equipment or the refrigerant lines based upon the degree of degradation of the residual material that was estimated in this manner.

PREFERRED EMBODIMENTS OF THE INVENTION

Figure 1:
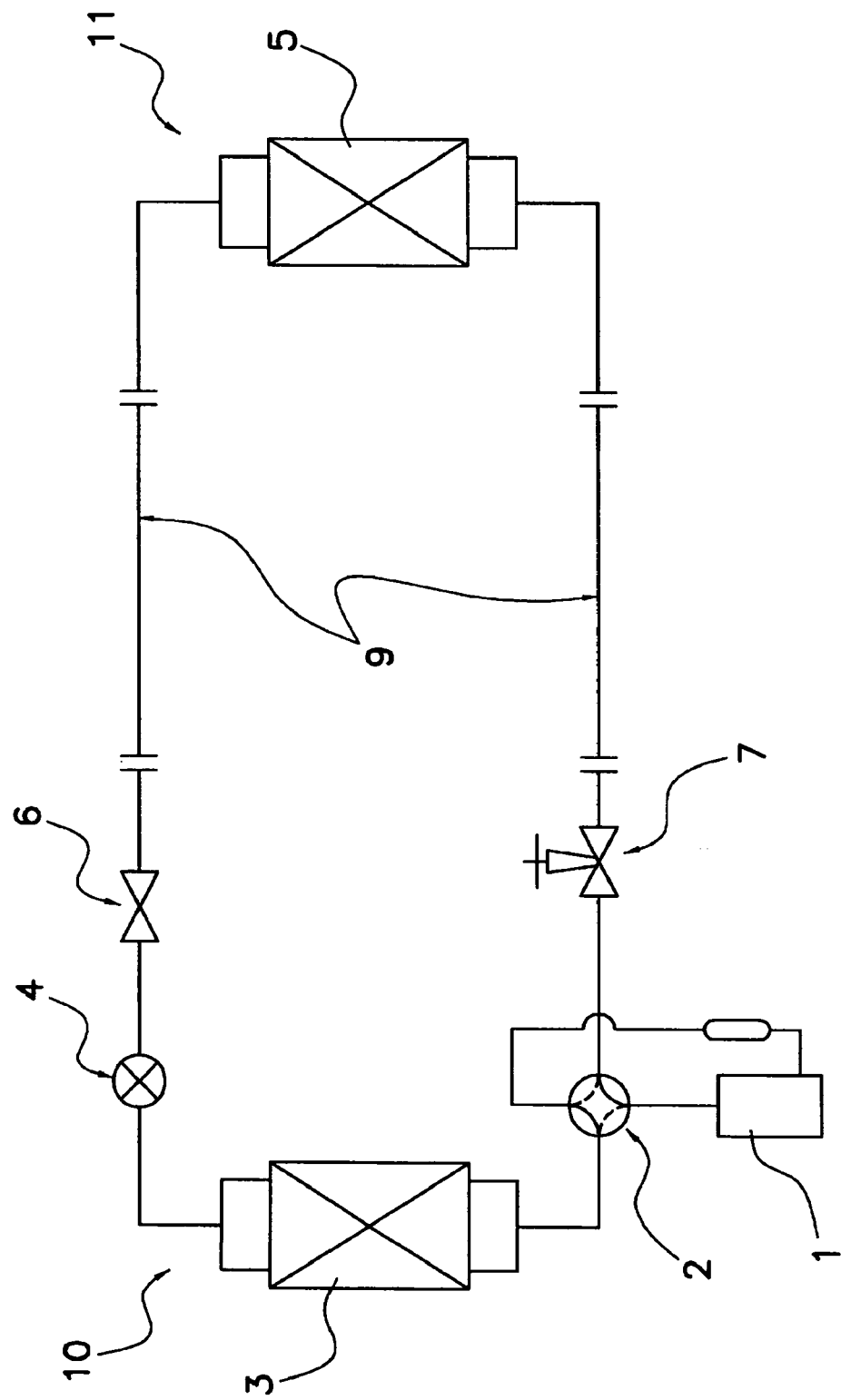
FIG. 1 is a circuit diagram of an air conditioner that includes refrigerant connection lines that are the object of a reuse determination.

FIG. 1 shows a refrigerant circuit diagram of an air conditioner having an outdoor unit 10 and an indoor unit 11. The discharge side and intake side of a compressor 1 are connected to a primary port of a four way switching valve 2. In addition, an outdoor heat exchanger 3, an expansion valve 4, and an indoor heat exchanger 5 are serially connected to a secondary port of the four way switching valve 2. In addition, a liquid cut-off valve 6 and a gas cut-off valve 7 are provided in the refrigerant circuit.

The outdoor unit 10 and the indoor unit 11 are connected together by means of refrigerant connection lines 9. These lines 9 are embedded in the walls or the rear side of the ceilings of an apartment building, an office building, a residential home having a central air conditioning system, and the like.

Many air conditioners that are installed in these types of buildings and the like currently use HCFC-22 as a refrigerant. When these air conditioners are to be replaced with air conditioners that use HFC type refrigerants, wasteful cleaning will no longer be performed and costs can be reduced if the determination method according to an embodiment of the present invention shown below is used.

<Method of Determining Whether or not Preexisting Lines Need Cleaning for Reuse>

When a preexisting air conditioner is to be removed, the liquid refrigerant is first sent to the outdoor heat exchanger 3 by means of a pump-down operation and the like and recovered. Although the refrigerant and the refrigerator oil inside the preexisting lines 9 are removed in this way, residual oil that at least includes small amounts of contaminants remains adhered to the inner surface of the lines 9.

Figure 2:
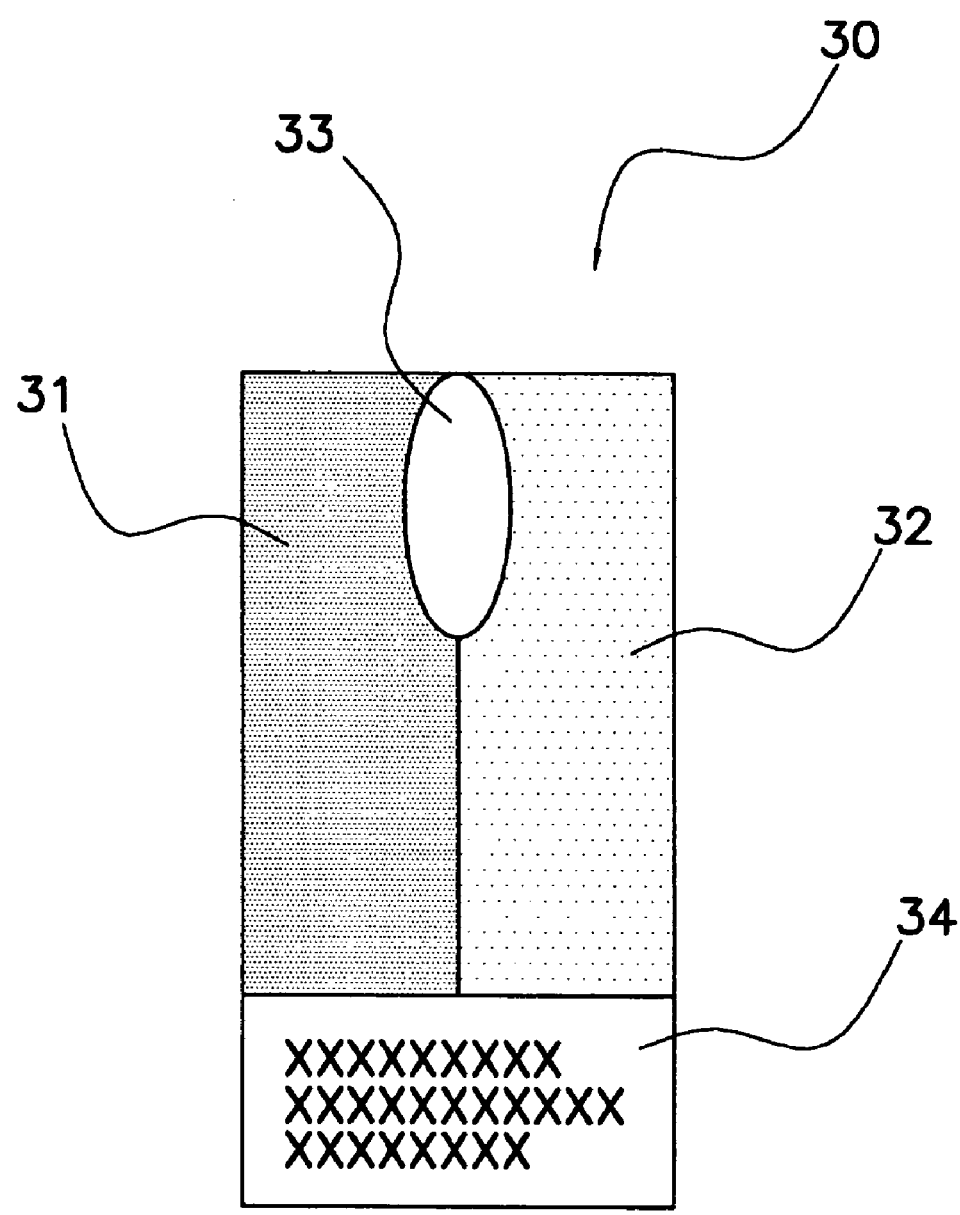
FIG. 2 is a plan view of a check sheet.

The degree to which this residual oil is fouled can be easily checked by means of a check sheet 30 shown in FIG. 2, and a determination with regard to the need to clean the preexisting lines 9 for reuse will be made.

The check sheet 30 is a small tool that is the size of a business card, and designed so that it can be used at the location in which the preexisting lines 9 are installed. This check sheet 30 is a tool in which a first portion 31 that shows a cleaning need reference color, a second portion 32 that shows a normal oil color, a collection portion 33 on which residual oil is applied, and an instruction portion 34 that shows instructions regarding use, are unitarily formed. The cleaning need reference color of the first portion 31 is a reference color to determine whether or not there is a need to clean the lines 9 when reusing the lines 9, and thus is a reference color that can determine that there is a need for cleaning if the color of the residual oil is dark, and can determine there is no need for cleaning if the color of the residual oil is light. The normal oil color of the second portion 32 shows the color of residual oil in which the lines 9 can be reused without cleaning. Thus, if the color of the residual oil is closer to the normal oil color of the second portion 32 than the cleaning need reference color of the first portion 31, the lines 9 can be reused without line cleaning. The first portion 31 and the second portion 32 are side by side, and are both disposed side by side with the collection portion 33.

The collection portion 33 of the check sheet 30 is formed from an absorbent cotton or cloth, and the residual oil inside the lines 9 will be applied thereto when, for example, a user wipes the inner surface of the lines 9 with the check sheet 30. By comparing the color of the residual oil applied to the collection portion 33 with the cleaning need reference color of the first portion 31, it can be determined whether or not cleaning is needed when reusing the lines 9.

When the outdoor unit 10 and the indoor unit 11 of a preexisting air conditioner are to be removed and the check sheet 30 is brought to the location of the air conditioner, a determination can easily be made with regard to the appropriation (reuse) of the preexisting refrigerant connection lines 9. A user will first press the collection portion 33 of the check sheet 30 onto the inner surface of the lines 9 to apply residual oil inside the lines 9 to the collection portion 33, and then will compare the color of the residual oil applied to the collection portion 33 to the cleaning need reference color of the first portion 31 and the normal oil color of the second portion 32. Then, if the color of the residual oil on the collection portion 33 is closer to the normal oil color of the second portion 32 than the cleaning need reference color of the first portion 31, the user can determine that line cleaning is not needed for the reuse of the lines 9, and if the color of the residual oil of the collection portion 33 is darker than the cleaning need reference color of the first portion 31, the user can determined that line cleaning is needed for the reuse of the lines 9.

Note that the cleaning need reference color of the first portion 31 and the normal oil color of the second portion 32 of the check sheet 30 are determined from large amounts of accumulated data on residual oil inside preexisting lines. If this check sheet 30 is used, it will be possible to correctly determine the need for line cleaning during the appropriation of preexisting lines with an extremely high degree of accuracy.

MERITS OF USING THE METHOD OF DETERMINING THE NEED FOR CLEANING OF THE PRESENT EMBODIMENT

[1]

In the past, it took time and a great deal of cost to confirm the degree of fouling of preexisting lines, and thus a method was adopted in which the task of confirming the degree of fouling was not done, and the preexisting lines were cleaned and reused without condition.

In contrast, if the determination method of the present embodiment is used, a simple check sheet 30 can be used on location (where the preexisting lines 9 are installed), and thus the need for line cleaning with respect to the reuse of the refrigerant connection lines 9 can be determined easily and with a high degree of accuracy.

Then, by using the check sheet 30 to check the preexisting refrigerant connection lines 9, when the residual oil inside the preexisting lines 9 is not particularly dirty and there is not need for cleaning, wasteful line cleaning can be omitted, and the cost of reusing the lines 9 can be reduced.

[2]

Here, the first portion 31 that shows the cleaning need reference color for determining the need for line cleaning is arranged on the check sheet 30, and the second portion 32 that shows the normal oil color is arranged on the check sheet 30. Thus, a user of the check sheet 30 can recognize that the color of the residual oil applied to the collection portion 33 is lighter than the cleaning need reference color of the first portion 31 and determine that line cleaning is not needed, and can recognize that the color of the residual oil applied to the collection portion 33 is closer to the normal oil color of the second portion 32 than the cleaning need reference color of the first portion 31 and can more accurately determine that line cleaning is not needed.

[3]

With the check sheet 30, the first portion 31, the second portion 32, and the collection portion 33 are disposed near each other, and thus the task of visually comparing the cleaning need reference color and the normal oil color with the residual oil applied to the collection portion 33 will be simplified.

Note that although there are some differences due to the type of refrigerator oil used in preexisting air conditioners, generally speaking, the cleaning need reference color of the first portion 31 will be red-orange having a small amount of black tint, and the normal oil color of the second portion 32 will be yellow-white having a reddish tint.

SITUATIONS IN WHICH THE RESIDUAL OIL INSIDE THE PREEXISTING LINES IS EXTREMELY DIRTY

With the check sheet 30 described above, the need for line cleaning can be determined based upon the color of the residual oil applied to the collection portion 33. If the color of the residual oil is slightly darker than the cleaning need reference color of the first portion 31, then a user of the check sheet 30 can decide to clean the preexisting lines 9 and reuse them.

Figure 3:
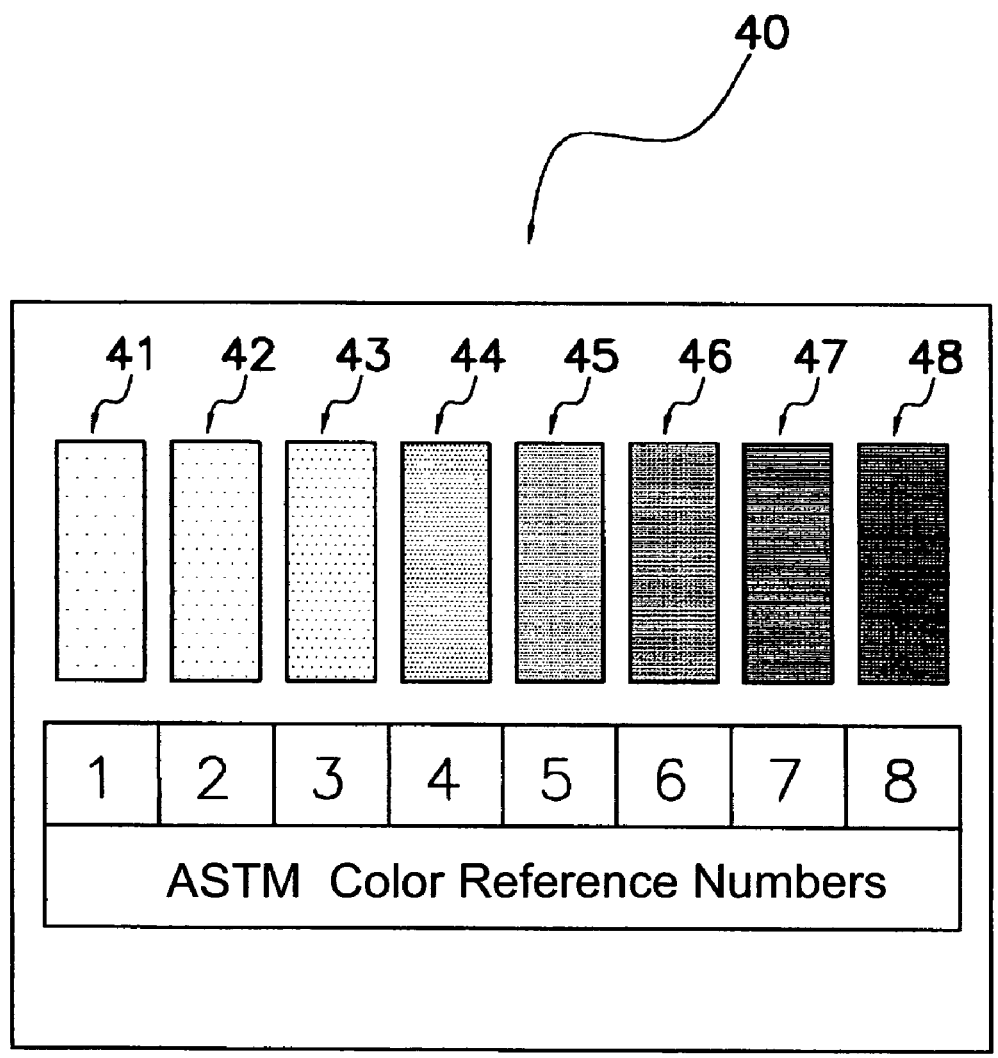
FIG. 3 is a plan view of a color sample table.

However, when the color of the residual oil applied to the collection portion 33 is extremely dark and it is thought that the deterioration of the residual oil is severe, the color sample table 40 shown in FIG. 3 will be used to determine whether the lines 9 can be reused or whether the lines 9 have to be discarded. In other words, it is preferable that the color sample table 40 be prepared in addition to the check sheet 30, and both be used to make a determination regarding the reuse of the preexisting refrigerant connection lines 9.

The color sample table 40 of FIG. 3 is a sheet on which are printed the ASTM (American Standard Test Method) color reference numbers, and color display portions 41–48 are disposed above color reference numbers 1–8. The color displayed on the color display portion 41 is light yellow, becomes more red as the color reference numbers increase, and the color displayed at color reference number 44 is orange. In addition, as the reference numbers increase, more red will be added and the colors will become darker. Then, the color displayed at color reference number 48 will be red-black. Note that the cleaning need reference color of the first portion 31 of the check sheet 30 corresponds to the color displayed at color reference number 44 of the color sample table 40.

A person checking the reusability of the lines 9 can determine that the lines 9 can be reused without cleaning when the color of the residual oil corresponds to the colors of the color reference numbers 1–3 of the color sample table 40, can determine that lines 9 which have been cleaned can be reused when the color of the residual oil corresponds to the colors of the color reference numbers 4–8, and can determine that the lines 9 cannot be reused when the color of the residual oil is darker than the color of color reference number 8 and the black tint thereof is strong. In other words, when the color of the residual oil applied to the collection portion 33 of the check sheet 30 is extremely dark and it is thought that the degradation of the residual oil is severe, the color of the color display portion 48 of the color sample table 40 will be compared to the color of the residual oil, and if the color of the residual oil is darker than the color of the color display portion 48 (the color of ASTM color reference number 8), then it can be decided to discard the preexisting lines 9 and install new refrigerant connection lines. This is mostly because when the color of the residual oil is darker than the color display portion 48 (the color of ASTM color reference number 8) and is a color that is close to black, abrasive powder and the like due to poor lubrication of the compressor friction members in the preexisting air conditioner is the main component of the black color of the residual oil, and accumulated material (foreign material) cannot be removed even if the compressor, the refrigerant system components, and the refrigerant lines are cleaned.

SITUATIONS IN WHICH THE COMPRESSOR OF A PREEXISTING AIR CONDITIONER STOPS OPERATING

In the past, even in situations in which the compressor stops operating, the preexisting lines will be cleaned and reused if not particularly old.

However, in situations in which the temperature inside the lines increases due to refrigerant leakage and the motor of the compressor burns out, there is a strong possibility that oxidation will continue to occur inside the lines, and thus it is not preferable that the refrigerant lines be used even if cleaned.

Even in this situation, it is effective to use the color sample table 40 to check the color of the residual oil as described above. If oxidation is continuing inside the lines 9, the color of the residual oil should change such that it will be blacker than the color of the ASTM color reference number 8.

Thus, if a determination method that uses the aforementioned check sheet 30 and the color sample table 40 is employed, then problems can be controlled such as the preexisting lines 9 being simply cleaned and reused despite the fact that the motor of the compressor 1 is burnt and the insides of the preexisting lines 9 are oxidized and cannot be used even if the lines are cleaned.

MODIFICATIONS (A)

Instead of the check sheet 30 and the color sample table 40, it is also possible to use litmus paper that changes color by means of acid or alkali to make a determination relating to the reuse of the preexisting lines 9. If a pH analysis tool such as litmus paper or the like is used, the value of the total acid number of the residual oil inside the lines 9 will be understood, and thus a determination as the reusability of the lines 9 or whether or not cleaning is needed when reusing the lines 9 can be performed. In particular, when a pH analysis tool such as litmus paper or the like is used, the oxidative degradation of the lines 9 (the generation of hydrofluoric acid, formic acid, hydrochloric acid, and the like) can be easily determined with good accuracy.

In addition, it is preferable that a determination relating to the reuse of the lines 9 that used a pH analysis tool such as litmus paper and the like be added as a supplement to a determination by means of the check sheet 30 and the color sample table 40. In this situation, the degree of degradation of the residual oil will be double checked, and the determination relating to the reuse of the lines 9 will be more accurate.

(B)

It is also possible for the check sheet 30 and the color sample table 40 of the aforementioned embodiment to be used, after the lines 9 are cleaned, in an inspection which checks whether or not the lines 9 are at a predetermined level of cleanliness. After the lines 9 which have been determined to be reusable are cleaned, a new air conditioner can be used with more peace of mind by using the check sheet 30 and the like to confirm the degree of fouling inside the lines 9.

(C)

Although the first portion 31 that shows the cleaning need reference color and the second portion 32 that shows the normal oil color are arranged on the aforementioned check sheet 30, a third portion that shows a disposal need reference color may be added to the check sheet 30 or may replace the second portion 32. The disposal need reference color corresponds to the color of oil that is more degraded than the cleaning need reference color of the first portion 31, and is a reference color for ascertaining whether the residual oil inside the lines 9 is so degraded that the lines 9 cannot be used even if cleaned, or whether the lines 9 can be reused by cleaning. Specifically, the disposal need reference color is close to the color of the aforementioned color display portion 48 (the color of ASTM color reference number 8) of the color sample table 40.

Thus, if a check sheet that shows the cleaning need reference color and the disposal need reference color is used, it can determine whether or not the lines 9 have to be disposed, even if the color sample table 40 is not used. In other words, a user that uses this check sheet will determine that the lines 9 cannot be used even if cleaned and have to be disposed of if the color of the residual oil inside the lines 9 that was applied to the collection portion 33 is darker than the disposal need reference color, and will determine that the lines 9 can be reused by means of cleaning them if the color of the collection portion 33 is darker than the cleaning need reference color and lighter than the disposal need reference color.

(D)

Although the first portion 31, the second portion 32, and the collection portion 33 are unitary on the aforementioned check sheet 30, it is also possible to use a tool in which the first portion 31, the second portion 32, and the collection portion 33 are separate entities.

In addition, a cotton swab, a rag, or the like that corresponds to the collection portion 33 may be used with the color sample table 40, and a determination with regard to the reuse of the lines 9 can be performed by means thereof.

(E)

The check sheet 30 and the color sample table 40 can also be used in a determination whether or not a removed preexisting air conditioner can be recycled or reused. This is because, although it will often be the case that the components of a preexisting air conditioner cannot be recycled at all if the residual oil of the line portions of the removed air conditioner are severely oxidized, there will also be times in which components other than the compressor can be reused when there is little fouling of the residual oil.

INDUSTRIAL APPLICABILITY

If a heat exchanger unit according to the present invention is used, the check tool can be used to easily determine the reusability of refrigerant using equipment or refrigerant lines by means of color, and problems such as wasteful cleaning when the interiors of refrigerant using equipment or refrigerant lines are not particularly dirty and there is no need for cleaning, and cleaning and reusing refrigerant using equipment or refrigerant lines despite the fact that the interiors thereof are fouled and cannot be used even if cleaned, will be controlled.

The invention claimed is:

1. A method of determining reusability of refrigerant using equipment or refrigerant lines, the method comprising the steps of:
   (a) applying residual material that remains inside the refrigerant using equipment or the refrigerant lines to a check tool, the check tool being applied inside the refrigerant using equipment of the refrigerant lines; and
   (b) performing a determination with regard to reusability of the refrigerant using equipment or the refrigerant lines based upon a color of the check tool on which the residual material was applied.

2. The method of determining the reusability of refrigerant using equipment or refrigerant lines disclosed in claim 1, wherein
   the check tool includes a first means on which the residual material will be applied, and second means that display a reference color that is a determination reference;
   the residual material is applied to the first means in step (a); and
   a color of the first means is compared to the reference color of the second means to perform the determination in step (b).

3. The method of determining the reusability of refrigerant using equipment or refrigerant lines disclosed in claim 2, wherein
   the second means of the check tool displays a plurality of reference colors.

4. The method of determining the reusability of refrigerant using equipment or refrigerant lines disclosed in claim 3, wherein
   the second means of the check tool displays a normal color that indicates that cleaning is unnecessary when using the refrigerant using equipment or the refrigerant lines, and a boundary color that indicates a boundary at which cleaning is necessary when using the refrigerant using equipment or the refrigerant lines.

5. The method of determining the reusability of refrigerant using equipment or refrigerant lines disclosed in claim 3, wherein
   the second means of the check tool displays a first boundary color that is a reference for determining whether or not there is a need to clean the refrigerant using equipment or the refrigerant lines, and the second boundary color is a reference for determining whether or not it is possible to use the refrigerant using equipment or the refrigerant lines.

6. A check tool that is used with the method of determining the reusability of the refrigerant using equipment or the refrigerant lines disclosed in claim 2 wherein
   the first means and the second means are disposed near each other and are unitary.

7. The method of determining the reusability of refrigerant using equipment or refrigerant lines disclosed in claim 1, wherein
   the check tool is a pH analysis tool that changes color by means of an acid or an alkali;
   the residual material is applied to the pH analysis tool in step (a); and
   the degree of degradation of the residual material is estimated from the color of the pH analysis tool to perform the determination in step (b).

8. A method of determining reusability of refrigerant using equipment or refrigerant lines, the method comprising the steps of:
   (a) applying residual material that remains inside the refrigerant using equipment or the refrigerant lines to a first section of a check tool, the check tool being applied inside the refrigerant using equipment of the refrigerant lines; and
   (b) performing a determination with regard to reusability of the refrigerant using equipment or the refrigerant lines based upon a plurality of reference colors of a second section of the check tool, the first section having a color that is compared to the reference colors of the second section to perform the determination in step (b), and the reference colors including a normal color that indicates that cleaning is unnecessary when using the refrigerant using equipment or the refrigerant lines and a boundary color that indicates a boundary at which cleaning is necessary when using the refrigerant using equipment or the refrigerant lines.

9. A method of determining reusability of refrigerant using equipment or refrigerant lines, the method comprising the steps of:
   (a) applying residual material that remains inside the refrigerant using equipment or the refrigerant lines to a first section of a check tool, the check tool being applied inside the refrigerant using equipment of the refrigerant lines; and
   (b) performing a determination with regard to reusability of the refrigerant using equipment or the refrigerant lines based upon a plurality of reference colors of a second section of the check tool, the first section having a color that is compared to the reference colors of the second section to perform the determination in step (b), and the reference colors including a first boundary color that is a reference for determining whether or not there is a need to clean the refrigerant using equipment or the refrigerant lines and a second boundary color that is a reference for determining whether or not it is possible to use the refrigerant using equipment or the refrigerant lines.

* * * * *